United States Patent
Klenke et al.

(10) Patent No.: US 10,238,544 B2
(45) Date of Patent: Mar. 26, 2019

(54) MARKING LENTICULES FOR REFRACTIVE CORRECTION

(75) Inventors: Jörg Klenke, Nürnberg (DE); Katrin Skerl, Bad Doberan (DE); Theo Seiler, Zürich (DE)

(73) Assignee: Wavelight GmbH (DE)

( * ) Notice: Subject to any disclaimer, the term of this patent is extended or adjusted under 35 U.S.C. 154(b) by 309 days.

(21) Appl. No.: 14/401,478

(22) PCT Filed: Jun. 7, 2012

(86) PCT No.: PCT/ER2012/060832
§ 371 (c)(1),
(2), (4) Date: Nov. 26, 2014

(87) PCT Pub. No.: WO2013/182245
PCT Pub. Date: Dec. 12, 2013

(65) Prior Publication Data
US 2015/0141971 A1 May 21, 2015

(51) Int. Cl.
*A61F 9/008* (2006.01)
*A61B 90/00* (2016.01)

(52) U.S. Cl.
CPC .......... *A61F 9/00836* (2013.01); *A61B 90/39* (2016.02); *A61F 9/00827* (2013.01); *A61B 2090/3912* (2016.02); *A61B 2090/3937* (2016.02); *A61B 2090/3983* (2016.02); *A61F 2009/00844* (2013.01); *A61F 2009/00872* (2013.01)

(58) Field of Classification Search
CPC .. A61F 9/008; A61F 9/00836; A61F 9/00827; A61F 2009/00844; A61F 2009/00872; A61F 90/39; A61F 2090/3912; A61F 2090/3937; A61F 2090/3983; A61B 90/39; A61B 2090/3912; A61B 2090/3937; A61B 2090/3983
See application file for complete search history.

(56) References Cited

U.S. PATENT DOCUMENTS

| | | | |
|---|---|---|---|
| 2004/0243112 A1* | 12/2004 | Bendett | A61F 9/00827 606/5 |
| 2008/0051772 A1* | 2/2008 | Suckewer | A61F 9/008 606/5 |
| 2009/0137988 A1 | 5/2009 | Kurtz | |
| 2009/0137991 A1 | 5/2009 | Kurtz | |
| 2010/0331830 A1* | 12/2010 | Bischoff | A61F 9/008 606/5 |
| 2012/0078240 A1 | 3/2012 | Spooner | |
| 2014/0155875 A1* | 6/2014 | Bergt | A61F 9/00827 606/5 |

FOREIGN PATENT DOCUMENTS

DE 102008049401 A1 4/2010

* cited by examiner

*Primary Examiner* — Lynsey C Eiseman
*Assistant Examiner* — Jessandra F Hough
(74) *Attorney, Agent, or Firm* — Keiko Ichiye, Esq.

(57) ABSTRACT

In certain embodiments, marking a lenticule includes controlling a focus of pulsed laser radiation having ultrashort pulses. A lenticule marking is created in a cornea of an eye with the pulsed laser radiation to mark the lenticule. The lenticule is then created in the cornea with the pulsed laser radiation.

14 Claims, 3 Drawing Sheets

MARKING LENTICULES FOR REFRACTIVE CORRECTION

CROSS REFERENCE TO RELATED APPLICATIONS

This application is a section 371 national stage phase of International Application No. PCT/EP2012/060832, filed 7 Jun. 2012, titled "MARKING LENTICULES FOR REFRACTIVE CORRECTION," which is hereby incorporated by reference in its entirety.

TECHNICAL FIELD

The present disclosure relates generally to corneal surgical devices, and more particularly to marking lenticules for refractive correction.

BACKGROUND

Refractive surgery uses lasers to reshape the cornea to correct refractive defects of the eye. According to some techniques, a flap of the eye is lifted to expose a portion of the cornea that is reshaped by ablation using an excimer laser. The flap is then replaced. According to other techniques, a femtosecond laser makes incisions in the cornea to create a lenticule. The lenticule is removed to reshape the cornea.

BRIEF SUMMARY

In certain embodiments, a device for marking a lenticule comprises a laser device and a control computer. The laser device is configured to create a lenticule in an eye using pulsed laser radiation having ultrashort pulses. The laser device includes one or more controllable components configured to control a focus of the pulsed laser radiation. The control computer is configured to instruct the one or more controllable components to create a lenticule marking in a cornea of an eye with pulsed laser radiation to mark a lenticule, and then create the lenticule in the cornea with the pulsed laser radiation.

In certain embodiments, a method for marking a lenticule includes controlling a focus of pulsed laser radiation having ultrashort pulses. A lenticule marking is created in a cornea of an eye with the pulsed laser radiation to mark the lenticule. The lenticule is then created in the cornea with the pulsed laser radiation.

In certain embodiments, a tangible computer-readable medium stores computer code for marking a lenticule that when executed by a computer is configured to control a focus of pulsed laser radiation having ultrashort pulses. The computer code is also configured to create a lenticule marking in a cornea of an eye with pulsed laser radiation to mark a lenticule, and then create the lenticule in the cornea with the pulsed laser radiation.

BRIEF DESCRIPTION OF THE DRAWINGS

Exemplary embodiments of the present disclosure will now be described by way of example in greater detail with reference to the attached figures, in which.

DESCRIPTION OF EXAMPLE EMBODIMENTS

Figure 1:
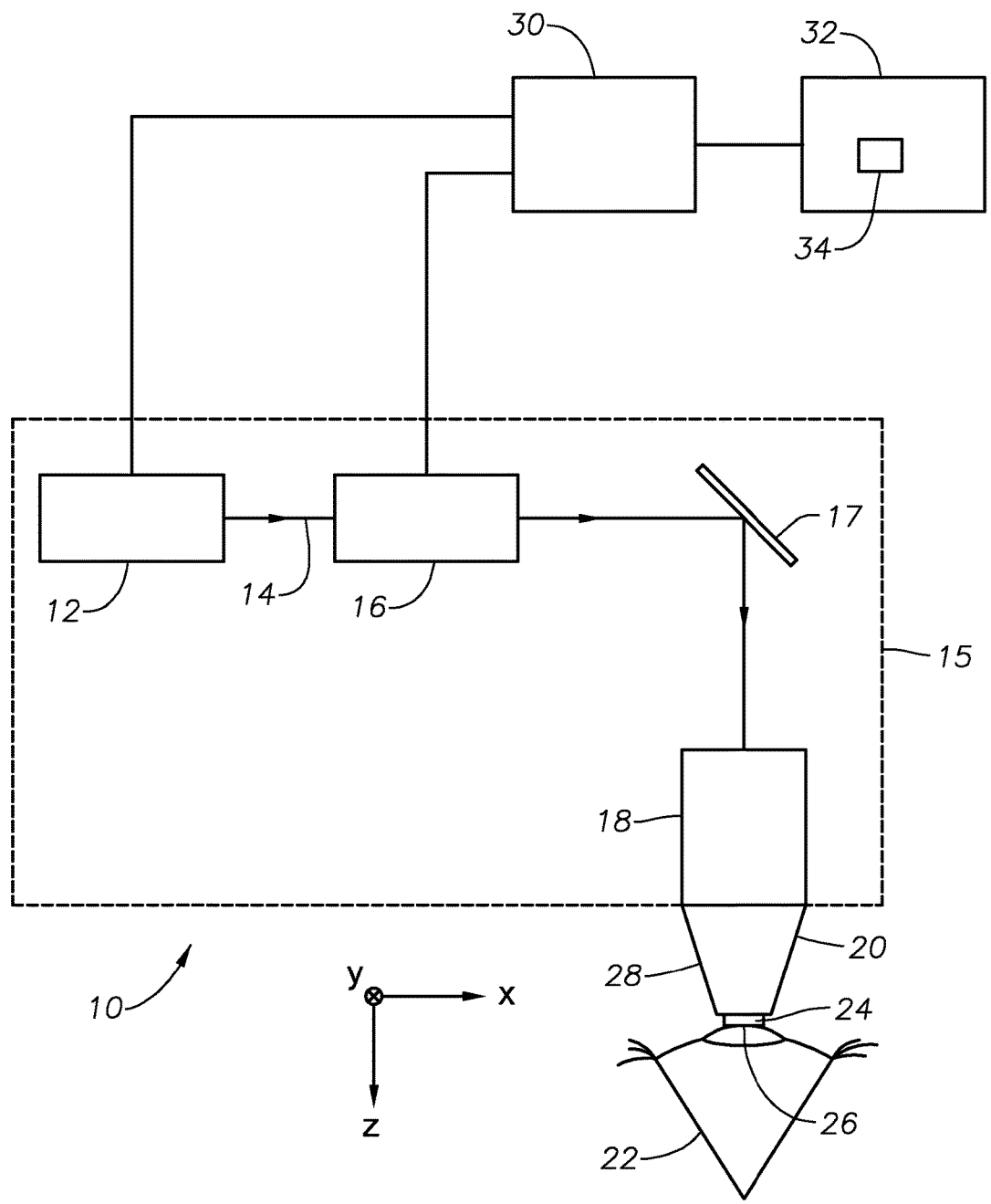
FIG. 1 illustrates an example of a device configured to perform refractive correction according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments. In addition, certain drawings may be in schematic form.

FIG. 1 illustrates an example of a device 10 configured to mark a lenticule according to certain embodiments. In the embodiments, the device 10 includes a laser device 15 and a control computer 30. The laser device 15 can create a lenticule marking in a cornea (such as the stroma) of an eye with pulsed laser radiation with ultrashort pulses (such as pico-, femto-, or attosecond pulses) to mark a lenticule. The laser device can then create a lenticule in the cornea with the pulsed laser radiation. The lenticule may be shaped according to a refractive correction profile such that when the lenticule is removed the refractive correction is applied. In certain embodiments, laser device can create a flap or removal incision in the cornea with the pulsed laser radiation to allow for removal of the lenticule. The lenticule marking may allow a surgeon to determine if the lenticule has been completely removed.

In the illustrated example of FIG. 1, the device 10 performs surgery on a sample 22. The device 10 includes a laser device 15, a patient adapter 20, a control computer 30, and a memory 32 coupled as shown. The laser device 15 may include a laser source 12, a scanner 16, one or more optical elements 17, and/or a focusing objective 18 coupled as shown. The patient adapter 20 may include a contact element 24 (which has an abutment face 26 disposed outwardly from a sample) and a sleeve 28 coupled as shown. The memory 32 stores a control program 34. The sample 22 may be an eye.

The laser source 12 generates a laser beam 14 with ultrashort pulses. In this document, an "ultrashort" pulse of light refers to a light pulse that has a duration that is less than a nanosecond, such as on the order of a picosecond, femtosecond, or attosecond. The focal point of the laser beam 14 may create a laser-induced optical breakdown (LIOB) in tissues such as the cornea. The laser beam 14 may be precisely focused to allow for precise incisions in the corneal cell layers, which may reduce or avoid unnecessary destruction of other tissue.

Examples of laser source 12 include femtosecond, picosecond, and attosecond lasers. The laser beam 14 may have any suitable wavelength, such as a wavelength in the range of 300 to 1500 nanometers (nm), for example, a wavelength in the range of 300 to 650, 650 to 1050, 1050 to 1250, or 1100 to 1500 nm. The laser beam 14 may also have a relatively small focus volume, e.g., 5 micrometers (μm) or less in diameter. In certain embodiments, the laser source 12 and/or delivery channel may be in a vacuum or near vacuum.

The scanner 16, optical elements 17, and focusing objective 18 are in the beam path. The scanner 16 transversely and longitudinally controls the focal point of the laser beam 14.

"Transverse" refers to a direction at right angles to the direction of propagation of the laser beam 14, and "longitudinal" refers to the direction of beam propagation. The transverse plane may be designated as the x-y plane, and the longitudinal direction may be designated as the z-direction. In certain embodiments, the abutment face 26 of the patient interface 20 is on an x-y plane.

The scanner 16 may transversely direct the laser beam 14 in any suitable manner. For example, the scanner 16 may include a pair of galvanometrically actuated scanner mirrors that can be tilted about mutually perpendicular axes. As another example, the scanner 16 may include an electro-optical crystal that can electro-optically steer the laser beam 14. The scanner 16 may longitudinally direct the laser beam 14 in any suitable manner. For example, the scanner 16 may include a longitudinally adjustable lens, a lens of variable refractive power, or a deformable mirror that can control the z-position of the beam focus. The focus control components of the scanner 16 may be arranged in any suitable manner along the beam path, e.g., in the same or different modular units.

One (or more) optical elements 17 direct the laser beam 14 towards the focusing objective 18. An optical element 17 may be any suitable optical element that can reflect, refract, and/or diffract the laser beam 14. For example, an optical element 17 may be an immovable deviating mirror. The focusing objective 18 focuses the laser beam 14 onto the patient adapter 20, and may be separably coupled to the patient adapter 20. The focusing objective 18 may be any suitable optical element, such as an f-theta objective.

Patient adapter 20 interfaces with the cornea of the eye 22. In the example, the patient adapter 20 has a sleeve 28 coupled to a contact element 24. The sleeve 28 couples to the focusing objective 18. The contact element 24 may be translucent or transparent to the laser radiation and has an abutment face 26 that interfaces with the cornea and may level a portion of the cornea. In certain embodiments, the abutment face 26 is planar and forms a planar area on the cornea. The abutment face 26 may be on an x-y plane, so the planar area is also on an x-y plane. In other embodiments, the abutment face 26 need not be planar, e.g., may be convex or concave.

The control computer 30 controls controllable components, e.g., the laser source 12 and scanner 16, in accordance with the control program 34. The control program 34 contains computer code that instructs the controllable components to focus the pulsed laser radiation at a region of the cornea to photodisrupt at least a portion of the region.

In certain examples of operation, the scanner 16 may direct the laser beam 14 to form incisions of any suitable geometry. Examples of types of incisions include bed incisions and lateral incisions. A bed incision is two-dimensional incision that is typically on an x-y plane. The scanner 16 may form a bed incision by focusing the laser beam 14 at a constant z-value under the abutment face 26 and moving the focus in a pattern in an x-y plane. A lateral incision is an incision that extends from under the corneal surface (such as from a bed incision) to the surface. The scanner 16 may form a lateral incision by changing the z-value of the focus of the laser beam 14 and optionally changing the x and/or y values.

Any suitable portion of the cornea may be photodisrupted. One or more of any of the corneal layers may be selected for photodisruption. In addition, a portion of a cell layer may be photodisrupted in the z-direction, but part of the cell layer may remain on the cornea. Moreover, a particular area (or "target zone") in the x-y plane may be selected for photodisruption. For example, a target zone that forms a bed incision may be photodisrupted.

The device 10 may photodisrupt a corneal layer in any suitable manner. In certain embodiments, the control computer 30 may instruct the laser device to focus the laser beam 14 at a constant z-value under the abutment face 26 and move in a pattern in the x-y plane that substantially covers the target zone. Any suitable pattern may be used. For example, according to a zigzag pattern, the scan path has a constant y-value and moves in the +x direction. When the scan path reaches a point of the border of the target zone, the path moves to a next y value that is a predetermined distance from the previous y-value and then moves in the −x direction until it reaches another point of the border. The scan path continues until the entire target zone is scanned. As another example, according to a spiral pattern, the scan path starts at or near the center of the target zone and moves in a spiral pattern until the path reaches the border of the target zone, or vice-versa.

Figure 2:
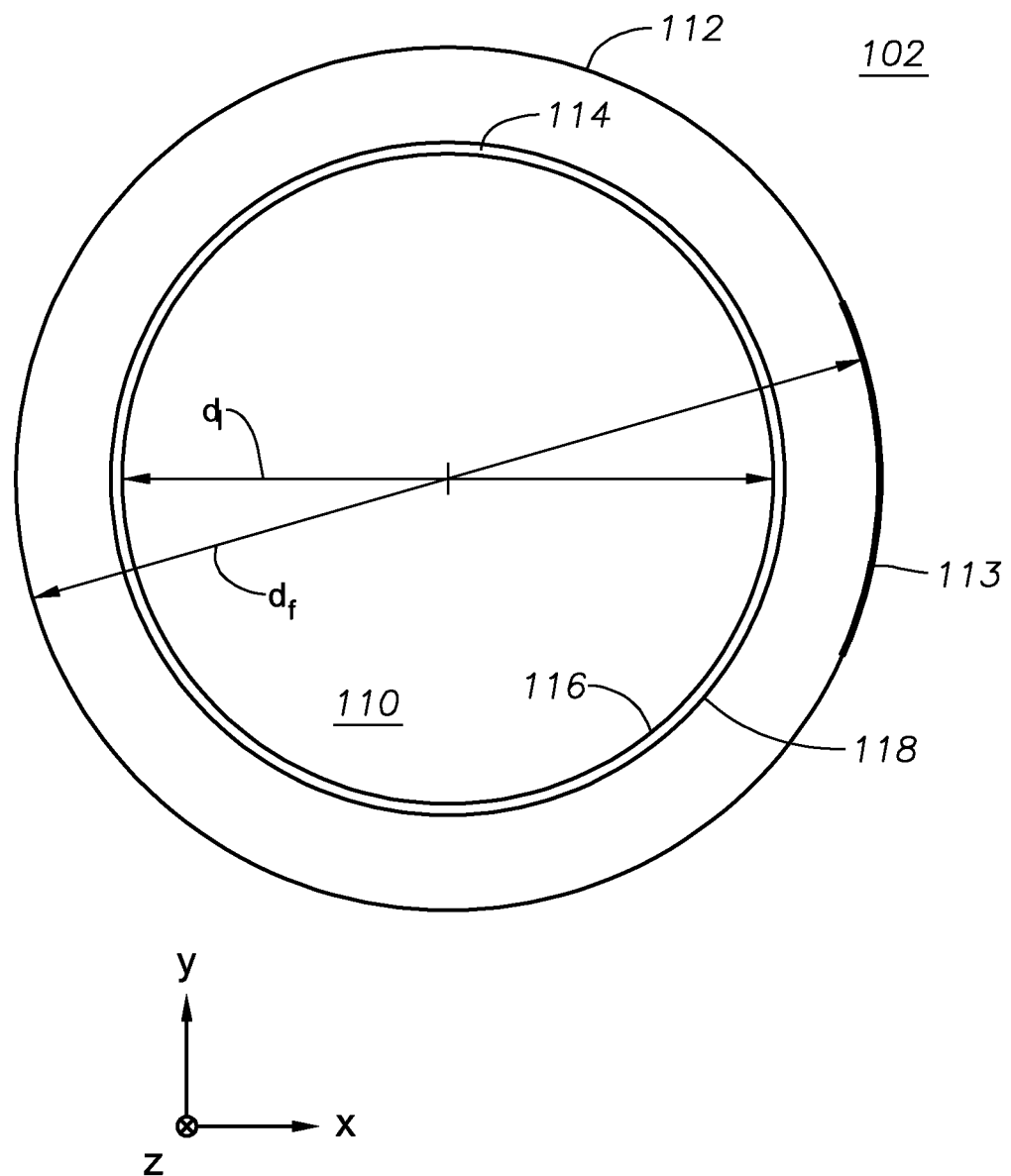
FIG. 2 illustrates a top view of an example of a lenticule marking according to certain embodiments.
Figure 3:
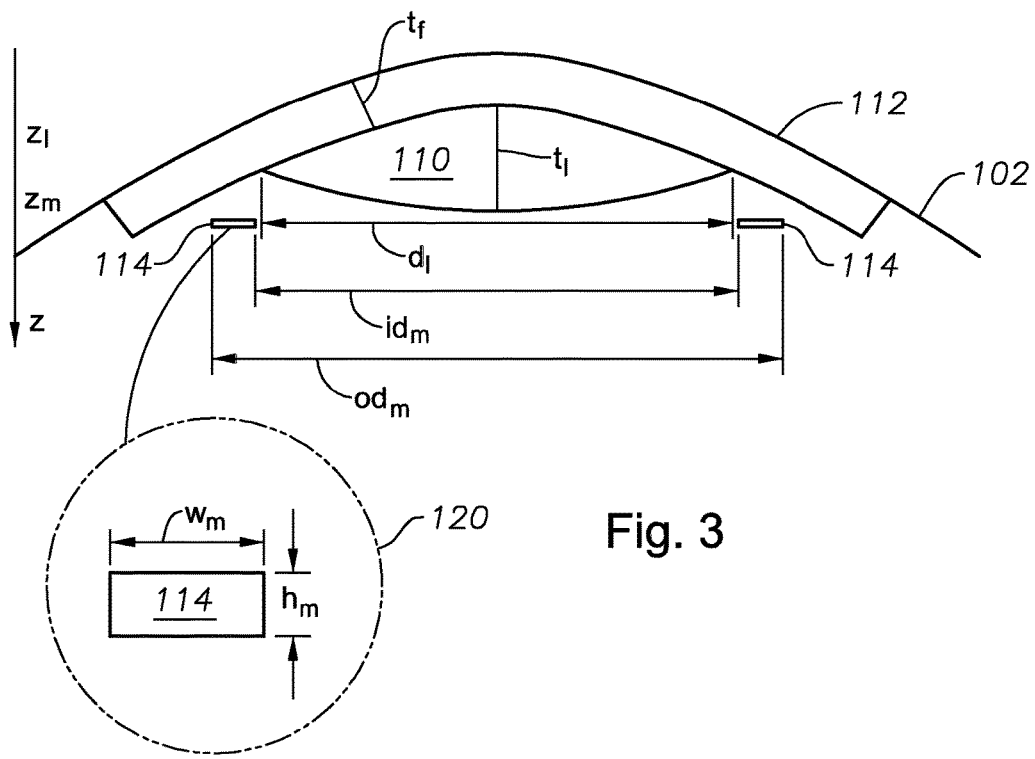
FIG. 3 illustrates a cross-section of an example of a lenticule marking according to certain embodiments.

FIGS. 2 and 3 illustrate an example of a lenticule marking 114 according to certain embodiments. FIG. 2 illustrates a top view of the lenticule marking 114, and FIG. 3 illustrates a cross-section of the lenticule marking 114.

A lenticule 110 can be created in the cornea (such as the stroma) and shaped according to a refractive correction profile such that when the lenticule 110 is removed the refractive correction is applied. In certain embodiments, a lenticule marking 114 may be created to serve as an outline for the lenticule 110. The lenticule 110 may then be created using the lenticule marking 114 as the outline. A flap 112 or removal incision 113 may then be created to allow for removal of the lenticule 110.

The lenticule 110 may have any suitable shape and size. In certain embodiments, the lenticule 110 may have a lens shape with any suitable perimeter shape, e.g., a circular, elliptical, free form, or irregular shape. The diameter $d_l$ of lenticule 110 may have any suitable value, such as a value in the range of 6 to 10 mm, such as approximately 8 mm. The thickness $t_l$ of lenticule 110 may have any suitable value, such as a value in the range of 5 µm to 200 µm, such as approximately 50 µm. The depth $z_l$ (measured from the surface of the eye in the z direction) of a center portion of the lenticule 110 may have any suitable value, such as a value less than 600 µm.

In the illustrated example, the lenticule marking 114 has an inner edge 116 (FIG. 2) with an inner diameter $id_m$ (FIG. 3) and an outer edge 118 (FIG. 2) with an outer diameter $od_m$ (FIG. 3). A cross-section 120 (FIG. 3) of the lenticule marking 114 shows the lenticule marking height $h_m$ and the lenticule marking width $w_m$. The lenticule marking 114 may have a depth $z_m$ (FIG. 3). The dimensions may describe the shape (e.g., perimeter shape), size (e.g., diameter), and location (e.g., x, y, z position) of the lenticule marking 114.

The lenticule marking 114 may have any suitable shape and size. In certain embodiments, the lenticule marking 114 may have a perimeter shape that substantially matches, e.g., is substantially the same shape as, the lenticule perimeter shape. In these embodiments, the lenticule marking 114 may serve as an outline of the lenticule 110. The height $h_m$ may have any suitable value, such as a value in the range of 1 to 20 to 50 or 50 to 100 µm. The width $w_m$ may have any suitable value, such as a value in the range of 0.5 to 50 to 100, 100 to 200, or 200 to 300 µm. Although the cross-section 120 is shown as a rectangle, the cross-section 120 may have any suitable shape, such as any a polygon, an ellipse, or a circle.

In certain embodiments, a particular portion of the lenticule marking 114 precisely marks the lenticule 110. For example, the inner edge 116 may be substantially the same as, slightly (e.g., 0 to 50 µm) smaller than, or slightly larger than the lenticule perimeter. As another example, the outer edge 118 may be substantially the same as, slightly smaller than, or slightly larger than the lenticule perimeter. Accordingly, the lenticule marking may allow a surgeon to determine if the lenticule has been completely removed.

The lenticule marking 114 may be created at any suitable location of the eye. In certain embodiments, the lenticule marking 114 may be created at any suitable depth. For example, the lenticule marking 114 may be created at a deeper depth $z_m$ than the depth $z_l$ of lenticule 114, such as 50 to 100, 100 to 200, or 200 to 300 µm deeper than depth $z_l$.

The flap 112 may have any suitable shape and size. In certain embodiments, the flap 112 may have any suitable perimeter shape, such as any of the shapes listed for the lenticule perimeter shape. The flap 112 may have any suitable size. In certain embodiments, the diameter $d_f$ of flap 112 may have a value larger than diameter $d_l$ of the lenticule 110, such as 5 to 10 mm. The thickness $t_f$ of flap 112 may have any suitable value, such as a value in the range of 60 to 510 µm.

The removal incision 113 may have any suitable shape and size. In certain embodiments, the removal incision 113 may be a lateral incision formed along at least a portion of where the perimeter of a flap 112 would be located if a flap 112 were used. The portion may have any suitable value, for example, a value in the range of ¹⁄₁₂ to ⅛, ⅛ to ¼, ¼ to ⅜, or ⅜ to ½.

Figure 4:
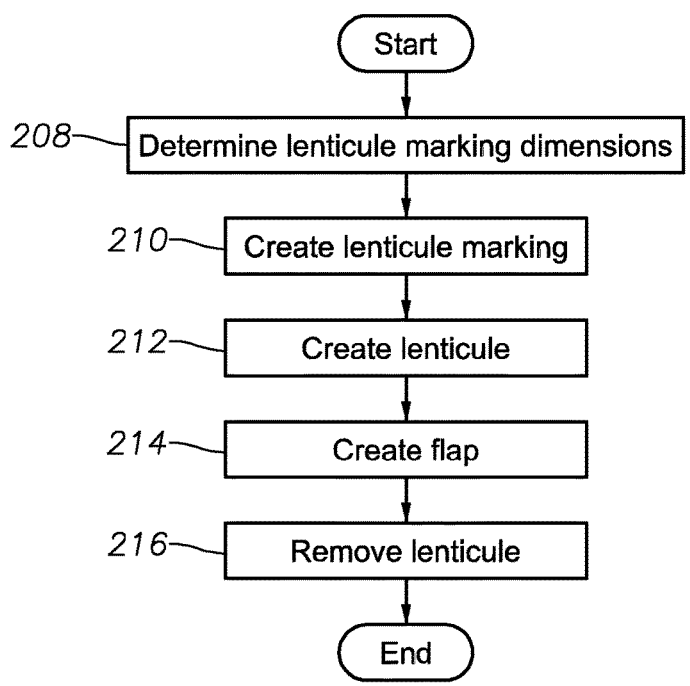
FIG. 4 illustrates an example of a method for creating a lenticule marking according to certain embodiments.

FIG. 4 illustrates an example of a method for creating a lenticule marking in a cornea of an eye according to certain embodiments. The method may be performed by the system 10 of FIG. 1.

The method starts at step 208, where the dimensions of the lenticule marking 114 are determined. In certain embodiments, system 10 may determine the dimensions for forming the lenticule marking 114. The dimensions may be determined in any suitable manner. As an example, a user may program the dimensions into system 10. As an example, system 10 may access the dimensions from another system.

As yet another example, system 10 may calculate the lenticule marking dimensions from a given lenticule 110. In a particular case, the lenticule marking perimeter shape may be substantially the same as the lenticule perimeter shape. For example, the inner edge 116 (or the outer edge 118) of the lenticule marking 114 may be substantially the same as the lenticule perimeter shape. In a particular case, the lenticule marking location may be determined from the lenticule location. For example, the lenticule marking 114 may have substantially the same x and y coordinates, but may have shallower, deeper, or the same z coordinates.

The lenticule marking 114 is created at step 210. The lenticule marking 114 may be created in any suitable manner. In the embodiments, the scanner 16 may direct the laser beam 14 to form a lenticule marking 114 according to the determined dimensions. The scanner 16 may form the marking 114 by focusing the laser beam 14 at a constant z-value under the abutment face 26 and moving the focus in the x-y plane in the shape of the marking. The scanner 16 may increase the height $h_m$ of the marking 114 in the z-direction by changing the z-value of the focus and moving the focus in the x-y plane in the shape of the marking 114.

The lenticule 110 is created at step 212. The lenticule 110 may be created in any suitable manner. In certain embodiments, the scanner 16 may direct the laser beam 14 to form the lenticule 110 by following the marking 114. The laser beam 14 may form the anterior side of the lenticule 110 by making a curved bed incision by moving in the x-y plane while changing the z-direction as needed to achieve the lenticule shape. The laser beam 14 may form the posterior side of the lenticule 110 in a similar matter.

In certain embodiments, the flap 112 is created at step 214. The flap 112 may be created in any suitable manner. In certain examples of operation, the scanner 16 may direct the laser beam 14 to form the flap 112. The anterior side of the lenticule 110 may form at least a portion of the bed of the flap 112. The laser beam 14 may form the rest of the bed and create a lateral incision around the perimeter of the flap 112. The scanner 16 may leave a portion of the perimeter uncut to form a hinge for the flap 112. In other embodiments, a removal incision 113 may be created instead of a flap 112. The removal incision 113 may be created by forming a lateral incision along at least a portion of where the perimeter of the flap 112 would be located, if a flap 112 were used.

The lenticule 110 is removed at step 216. The lenticule 110 may be removed through a flap 112 or removal incision 113. The lenticule 110 may be manually or automatically removed. The method then ends.

A component (such as the control computer 30) of the systems and apparatuses disclosed herein may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video or Versatile Disk (DVD)), database and/or network storage (for example, a server), and/or other computer-readable media.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A device for marking a lenticule, the device comprising:
    a laser device configured to create a lenticule in the cornea of an eye and a lenticule marking below and isolated from the lenticule in the cornea of the eye using pulsed laser radiation having a plurality of ultrashort pulses, the laser device comprising one or more controllable components configured to control a focus of the pulsed laser radiation; and
    a control computer configured to instruct the one or more controllable components to:
        determine a lenticule perimeter shape of the lenticule;
        create a removal incision in the cornea with the pulsed laser radiation;
        establish a lenticule marking perimeter shape of the lenticule marking, the lenticule marking perimeter shape having an inner diameter and an outer diameter, wherein one of the inner diameter and the out diameter substantially matches the lenticule perimeter shape such that the lenticule marking allows a surgeon to detect the lenticule perimeter shape;
        determine a lenticule depth of the lenticule;
        calculate a marking depth of the lenticule marking as 50 to 300 micrometers (μm) deeper than the lenticule depth;
        create the lenticule marking at the marking depth in the cornea with the pulsed laser radiation, the lenticule marking having the marking perimeter shape, wherein the lenticule marking is isolated from the lenticule and the removal incision;
        create a flap in the cornea with the pulsed laser radiation, the flap having a diameter larger than the outer diameter of the lenticule marking perimeter;
        create the lenticule in the cornea with the pulsed laser radiation,
    wherein the lenticule marking allows a surgeon to determine when the lenticule has been completely removed through the flap in the cornea.

2. The device of claim 1, the control computer further configured to instruct the one or more controllable components to:
    create a removal incision in the cornea with the pulsed laser radiation.

3. The device of claim 1, a marking width is between 0.5 to 300 micrometers (μm).

4. The device of claim 1, a marking height is between 1 to 100 micrometers (μm).

5. The device of claim 1, an ultrashort pulse being less than one (1) nanosecond.

6. A method for creating a lenticule in the cornea of an eye and a lenticule marking below and isolated from the lenticule, the method comprising:
    controlling a focus of pulsed laser radiation having a plurality of ultrashort pulses;
    determining a lenticule perimeter shape of the lenticule;
    creating a removal incision in the cornea with the pulsed laser radiation;
    establishing a lenticule marking perimeter shape of a lenticule marking, the lenticule marking perimeter shape having an inner diameter and an outer diameter, wherein one of the inner diameter and the out diameter substantially matches the lenticule perimeter shape such that the lenticule marking allows a surgeon to detect the lenticule perimeter shape;
    determining a lenticule depth of the lenticule;
    calculating a marking depth of the lenticule marking as 50 to 300 micrometers (μm) deeper than the lenticule depth;
    creating the lenticule marking in a cornea of an eye with the pulsed laser radiation at the marking depth to mark the lenticule, the lenticule marking having the marking perimeter shape, wherein the lenticule marking is isolated from the lenticule and the removal incision;
    creating a flap in the cornea with the pulsed laser radiation, the flap having a diameter larger than the outer diameter of the lenticule marking perimeter; and
    creating the lenticule in the cornea with the pulsed laser radiation,
    wherein the lenticule marking allows a surgeon to determine when the lenticule has been completely removed through the flap in the cornea.

7. The method of claim 6, further comprising:
    creating a removal incision in the cornea with the pulsed laser radiation.

8. The method of claim 6, a marking width is between 0.5 to 300 micrometers (μm).

9. The method of claim 6, a marking height is between 1 to 100 micrometers (μm).

10. The method of claim 6, an ultrashort pulse being less than one (1) nanosecond.

11. One or more tangible computer-readable media storing computer code for creating a lenticule in the cornea of an eye and a lenticule marking below and isolated from the lenticule that when executed by a computer is configured to:
    control a focus of pulsed laser radiation having a plurality of ultrashort pulses;
    determine a lenticule perimeter shape of the lenticule;
    create a removal incision in the cornea with the pulsed laser radiation;
    establish a lenticule marking perimeter shape of the lenticule marking, the lenticule marking perimeter shape having an inner diameter and an outer diameter, wherein one of the inner diameter and the out diameter substantially matches the lenticule perimeter shape such that the lenticule marking allows a surgeon to detect the lenticule perimeter shape;

determine a lenticule depth of the lenticule;

calculate a marking depth of the lenticule marking as 50 to 300 micrometers (μm) deeper than the lenticule depth;

create the lenticule marking in a cornea of an eye with pulsed laser radiation at the marking depth to mark a lenticule, the lenticule marking having the marking perimeter shape, wherein the lenticule marking is isolated from the lenticule and the removal incision;

create a flap in the cornea with the pulsed laser radiation, the flap having a diameter larger than the outer diameter of the lenticule marking perimeter; and create the lenticule in the cornea with the pulsed laser radiation, wherein the lenticule marking allows a surgeon to determine when the lenticule has been completely removed through the flap in the cornea.

12. The media of claim 11, further configured to:

create a removal incision in the cornea with the pulsed laser radiation.

13. The media of claim 11, a marking width is between 0.5 to 300 micrometers (μm).

14. The media of claim 11, a marking height is between 1 to 100 micrometers (μm).

* * * * *

UNITED STATES PATENT AND TRADEMARK OFFICE
CERTIFICATE OF CORRECTION

PATENT NO. : 10,238,544 B2
APPLICATION NO. : 14/401478
DATED : March 26, 2019
INVENTOR(S) : Klenke et al.

Page 1 of 1

It is certified that error appears in the above-identified patent and that said Letters Patent is hereby corrected as shown below:

On the Title Page

Item (86) PCT No. reading "PCT/ER2012/060832" should read --PCT/EP2012/060832--.

Signed and Sealed this
Seventh Day of May, 2019

Andrei Iancu
*Director of the United States Patent and Trademark Office*